United States Patent [19]

Myers

[11] Patent Number: 5,567,881
[45] Date of Patent: Oct. 22, 1996

[54] METHOD AND APPARATUS FOR INSPECTING A STRUCTURAL PART HAVING SURFACE IRREGULARITIES

[75] Inventor: Eugene A. Myers, St. Charles, Mo.

[73] Assignee: McDonnell Douglas Corporation, St. Louis, Mo.

[21] Appl. No.: 435,580

[22] Filed: May 5, 1995

[51] Int. Cl.$^6$ ............................ G01N 24/00; G01N 29/00
[52] U.S. Cl. ............................ 73/629; 73/588; 73/596; 73/634; 73/640; 73/643; 73/644
[58] Field of Search ............................ 73/618, 619, 621, 73/627, 629, 632, 633, 634, 640, 644, 866.5, 582, 584, 587, 588, 596, 620, 643; 324/262, 226; 33/501; 356/376, 379, 380

[56] References Cited

U.S. PATENT DOCUMENTS

| | | | |
|---|---|---|---|
| 3,566,479 | 3/1971 | Pascoe et al. | 33/503 |
| 3,624,711 | 11/1971 | Zeutschel | 73/627 |
| 4,161,885 | 7/1979 | Sack et al. | 73/597 |
| 4,274,289 | 6/1981 | Weiss et al. | 73/618 |
| 4,612,808 | 9/1986 | McKirdy et al. | 73/640 |
| 4,774,842 | 10/1988 | Kollar et al. | 73/640 |
| 4,881,177 | 11/1989 | McClean et al. | 73/634 |
| 4,894,806 | 1/1990 | Jen et al. | 73/625 |
| 5,038,615 | 8/1991 | Trulson et al. | 73/597 |
| 5,099,693 | 3/1992 | Payne et al. | 73/632 |
| 5,205,047 | 4/1993 | Danielli | 33/542 |
| 5,214,379 | 5/1993 | Chern | 324/220 |
| 5,247,251 | 9/1993 | Yost et al. | 324/220 |
| 5,426,980 | 6/1995 | Smith | 73/644 |

FOREIGN PATENT DOCUMENTS

| | | | |
|---|---|---|---|
| 376712 | 8/1968 | U.S.S.R. | 73/644 |
| 2011219 | 7/1929 | United Kingdom | 73/644 |
| WO8701269 | 3/1987 | WIPO | 73/644 |

OTHER PUBLICATIONS

*If It Moves -> Seal It With Brush*, Seal E-Z Corporation.
*Device for Ultrasound Scanning of Curved Object*, NASA Tech Briefs, vol. 19, No. 2, Feb., 1995, p. 50.

*Primary Examiner*—Hezron E. Williams
*Assistant Examiner*—Richard A. Moller
*Attorney, Agent, or Firm*—Bell, Seltzer, Park & Gibson, P.A.

[57] ABSTRACT

An inspection apparatus and associated method includes a sensor housing defining an internal cavity in which a sensor is at least partially disposed for inspecting the surface of a structural part and for detecting defects in the surface and the substructure of the part. The inspection apparatus includes a plurality of compliant fibers extending outwardly from a first end of the sensor housing and circumferentially about an opening defined by the first end of the sensor housing. The compliant fibers support the sensor housing above the surface of the part and maintain the sensor in a predetermined position relative to the surface of the part. The plurality of compliant fibers are adapted to flex laterally to accommodate obstructions on the surface of the part, such as raised fasteners, doublers or lap joints while maintaining the sensor in the predetermined position relative to the surface of the part. Consequently, the sensor can continue to acquire accurate signals which indicate the presence of structural defects in the surface and the substructure of the part as the inspection apparatus moves over the obstructions which protrude upwardly from the surface of the part.

13 Claims, 3 Drawing Sheets

METHOD AND APPARATUS FOR INSPECTING A STRUCTURAL PART HAVING SURFACE IRREGULARITIES

FIELD OF THE INVENTION

The invention relates to nondestructive testing (NDT) of a structural part. More particularly, the invention relates to a method and apparatus for inspecting a structural part having surface irregularities.

BACKGROUND OF THE INVENTION

Many structural parts must be inspected after manufacture and at regular intervals during their service lives to prevent unexpected failures. For example, metallic parts are subject to strength degradation due to fatigue cracks and corrosion that occur over time. Accordingly, NDT methods have been developed for inspecting the substructure of structural parts and areas that are not accessible to visible inspection.

The use of laminated composite parts in aircraft and automotive structures has increased dramatically because of their high strength and low weight. Laminated composites, however, are subject to internal flaws such as delamination, subsurface micro-cracking and voids which cannot be detected by surface inspection. Accordingly, structural parts made of laminated composite materials likewise must be inspected at regular intervals using NDT methods to avoid unexpected failures of critical parts.

A number of NDT methods are known for inspecting metallic and laminated composite parts. In addition, life extension programs for aging aircraft require the interrogation and validation of metallic parts to assure that fatigue cracks and corrosion do not compromise the strength of the structure. Some methods, such as ultrasonic resonance, require direct contact between the sensor and the surface of the part. Other NDT methods, such as ultrasonic pulse echo, require an intermediary fluid medium, commonly referred to as the couplant, which has a density greater than air. Still other NDT methods, such as eddy current and laser, do not require direct contact between the sensor and the part or the use of a couplant.

When NDT methods that do not require direct contact are used, it is important to maintain the distance of the sensor from the surface of the part, referred to as the standoff distance of the sensor, constant. Fluctuations in the standoff distance can result in false indications of the presence and magnitude of subsurface flaws. It is also important to maintain the angle of the sensor relative to the surface of the part, referred to as the orientation of the sensor, constant. Typically, the sensor is maintained normal to the surface, but in certain applications it may be desirable to scan the surface at an acute or obtuse angle. Nevertheless, variations in the orientation of the sensor likewise can result in erroneous readings.

A hand-held NDT apparatus for inspecting the substructure of metallic and laminated composite parts is disclosed in U.S. Pat. No. 4,774,842 issued to Kollar et al. and assigned to the assignee of the present invention. The apparatus includes a plurality of ultrasonic transducers mounted in a housing and electrically connected to a device for displaying a pulse echo signal. The housing has wheels to enable an operator to roll the apparatus longitudinally over the surface of the part to be inspected.

As the apparatus is rolled longitudinally, the transducers are mechanically moved back and forth laterally within the housing while emitting ultrasonic waves. The transducers are held against the surface of the part and oriented such that the ultrasonic waves are maintained normal to the surface regardless of the curvature of the surface. Thus, the area of the part under the path of the apparatus is inspected for subsurface flaws.

A number of structural parts, however, have irregular surfaces that include obstructions such as raised fasteners, doublers, or lap joints. For example, aircraft wing structures may include round-head fasteners that are not flush with the surface of the part. The apparatus disclosed in the Kollar et al. patent cannot be used to inspect a structural part having obstructions on the surface because the ultrasonic transducers and the housing are in close proximity to the surface of the part. As a result, the transducers and the housing may come in contact with an obstruction.

If a transducer contacts an obstruction, the transducer may be damaged or the standoff distance and/or the orientation of the sensor may be altered. If the housing comes in contact with an obstruction, the transducers may not get close enough horizontally to the obstruction to adequately inspect the surface and substructure of the part in the vicinity of the obstruction.

Lifting and moving the transducers and the housing over the obstruction is time consuming and may result in a change in the location and alignment of the transducers. Further, when using a couplant, relocating the apparatus to a new location on the surface of the part may result in a significant loss of the couplant.

SUMMARY OF THE INVENTION

In view of the noted deficiencies in the prior art it is an object of the invention to provide an improved method and apparatus for supporting a sensor above the surface of a structural part.

It is another object of the invention to provide a method and apparatus for inspecting a structural part having obstructions on the surface of the part.

It is another object of the invention to provide an NDT apparatus including a sensor for inspecting a structural part wherein a predetermined standoff distance of the sensor is maintained.

It is another object of the invention to provide an NDT apparatus including a sensor for inspecting a structural part wherein a predetermined orientation of the sensor is maintained.

It is another object of the invention to provide an NDT apparatus including a sensor and a couplant for inspecting a structural part wherein the couplant is substantially retained within the sensor housing even when the apparatus is moved over an obstruction on the surface of the part.

It is another object of the invention to provide a mechanical means for compliantly supporting the sensor of an NDT apparatus at a predetermined standoff distance above the surface of a structural part.

These and other objects are provided, according to the invention, by a method and apparatus for inspecting a structural part having obstructions on the surface, such as raised fasteners, doublers and lap joints. The apparatus supports a sensor at a predetermined position relative to the surface of the part with a plurality of compliant fibers which are arranged to contact the surface of the part and to flex laterally to accommodate the surface obstructions while maintaining the sensor in the predetermined position. Consequently, the sensor can continuously acquire accurate signals that indicate the presence of structural flaws in the part as the inspection apparatus is moved over the surface obstructions.

The method and apparatus of the present invention also generally includes compliant fiber support means for fixing the plurality of compliant fibers relative to the sensor such that the plurality of compliant fibers support the sensor above the surface of the part. In particular, the plurality of compliant fibers support the sensor in the predetermined position, such as a predetermined standoff distance and orientation, relative to the surface of the part.

According to one aspect of the invention, the apparatus is embodied by an NDT inspection apparatus. In this embodiment, the compliant fiber support means includes a sensor housing defining an internal cavity in which the sensor is at least partially disposed. A plurality of compliant fibers extend outwardly from a first end of the sensor housing and circumferentially about an opening formed in the first end of the sensor housing. The plurality of compliant fibers support the sensor housing above the surface of the structural part and maintain the sensor in the predetermined position relative to the surface of the part.

The plurality of compliant fibers have a predetermined compressive stiffness and a predetermined bending stiffness. The predetermined compressive stiffness of the fibers is preferably sufficient to support the weight of the apparatus and the downward force applied to the apparatus during an inspection. The predetermined bending stiffness of the fibers is preferably sufficient to overcome the frictional force applied to the apparatus during an inspection but pliant enough to flex laterally to accommodate the surface obstructions while continuously supporting the sensor and the sensor housing above the surface of the part.

Each compliant fiber extends longitudinally from a first end to an opposed second end. In one embodiment, each compliant fiber is secured adjacent the first end of the sensor housing such that the respective second ends of the plurality of compliant fibers extend a first predetermined distance beyond the first end of the sensor housing. Thus, the plurality of compliant fibers support the sensor at a second predetermined distance, or standoff distance, above the surface of the part to maintain the accuracy of the inspection method used. In addition, by supporting the sensor at the second predetermined distance above the surface of the part, the sensor is protected from damage due to contact with the surface obstructions on the part.

The plurality of fibers may be disposed in a plurality of circumferentially extending layers about the opening formed in the first end of the sensor housing. For example, in a preferred embodiment, the sensor housing is generally cylindrical such that the plurality of compliant fibers define a compliant fiber ring including a number of circumferentially extending compliant fibers layers. The plurality of compliant fibers, however, may define any shape, such as rectangular or square, that conforms to the opening formed in the sensor housing.

Irrespective of the shape of the sensor housing, in a preferred embodiment the plurality of compliant fibers and the internal cavity defined by the sensor housing may define a fluid reservoir. In this embodiment, the inspection apparatus may also include a fluid medium, such as water, oil or gel, disposed within the fluid reservoir and acting as a couplant for transmitting the signals generated by the sensor between the sensor and the part. In addition, the plurality of compliant fibers significantly reduces the loss of the fluid medium from the reservoir when the apparatus passes over a surface obstruction. Accordingly, the fluid medium requirements of the apparatus are substantially reduced for an inspection method that requires the use of a couplant.

In another preferred embodiment, the apparatus of the invention includes a sensor housing support assembly for permitting rotation of the sensor housing about at least two mutually perpendicular axes. Thus, the apparatus can inspect structural parts having a surface with a compound curvature while maintaining the sensor in the predetermined orientation relative to the surface of the part.

The sensor housing support assembly may also include biasing means, such as a spring, for urging the sensor housing against the surface of the part. In particular, the biasing means may be a rotational spring for urging the sensor housing about a third axis parallel to the surface of the part such that the respective second ends of the plurality of compliant fibers contact the surface of the part. At the same time, however, the plurality of compliant fibers continue to support the sensor at the predetermined standoff distance and in the predetermined orientation due to the predetermined compressive stiffness of the fibers.

Typically, the longitudinal movement of the apparatus is manually controlled by an operator and the lateral movement of the apparatus is automatically controlled by a scanner. In a preferred embodiment, however, the apparatus may include a controller means for moving the sensor longitudinally over the surface of the part according to a predetermined pattern. Thus, the inspection of a structural part having surface irregularities can be entirely automated.

In operation, the plurality of compliant fibers support a sensor at a predetermined standoff distance and a predetermined orientation relative to the surface of a structural part such that the sensor can accurately inspect the surface and substructure of the part. The plurality of compliant fibers are adapted to flex laterally to accommodate surface obstructions, such as raised fasteners, doublers and lap joints, while maintaining the predetermined standoff distance and the predetermined orientation of the sensor. Thus, the method and apparatus of the invention can inspect a structural part to detect, for example, fatigue cracks and corrosion in metallic parts and delaminations, micro-cracks and voids in laminated composite parts, which occur in the vicinity of a surface obstruction. Accordingly, structural defects in critical parts can be detected and the part repaired or replaced prior to an unexpected failure.

BRIEF DESCRIPTION OF THE DRAWINGS

The foregoing and other objects, advantages and features of the invention will become readily apparent in view of the following detailed description in conjunction with the accompanying drawings which illustrate preferred embodiments of the invention, and in which.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete and will fully convey the scope of the invention to those skilled in the art. Like numbers refer to like elements throughout.

Figure 1:
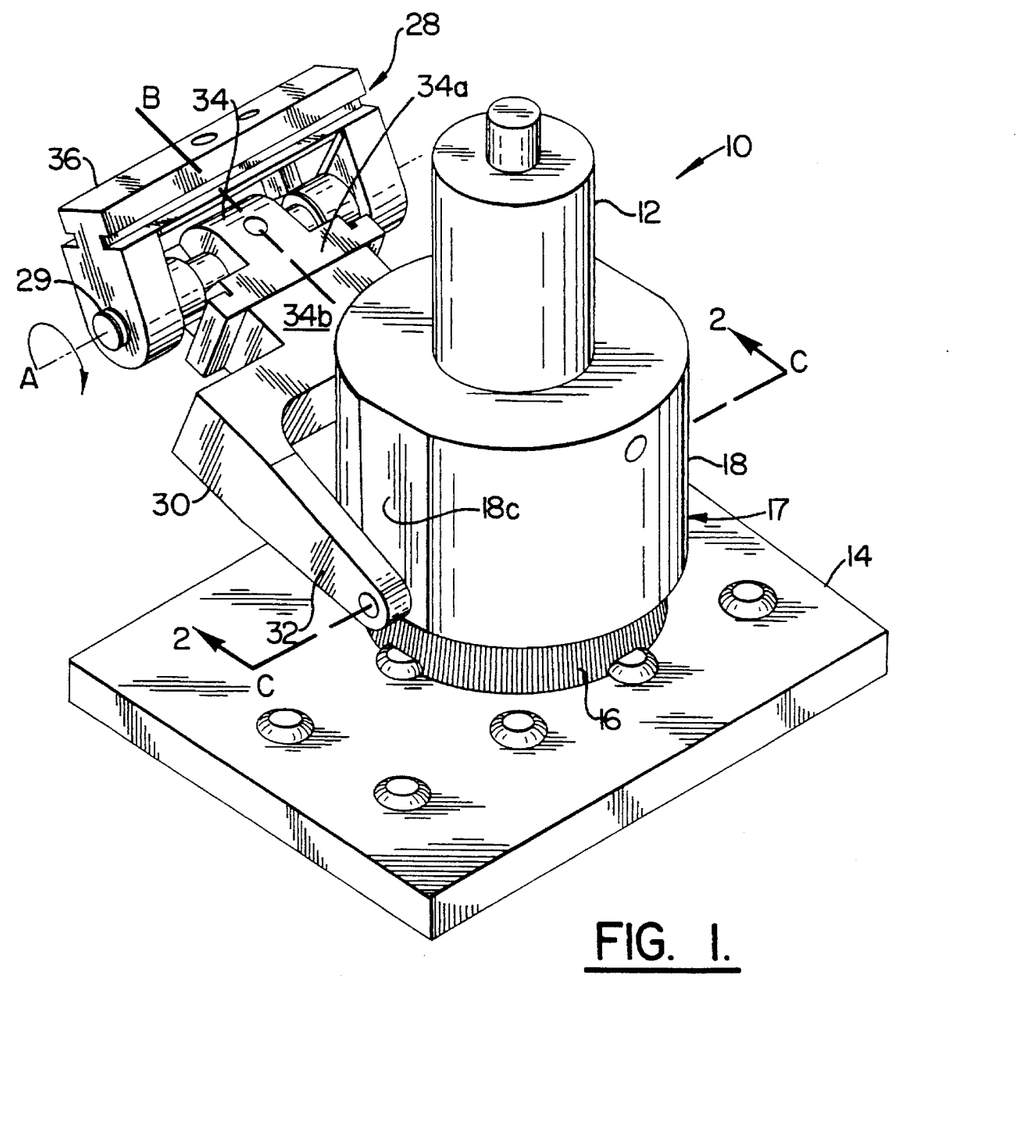
FIG. 1 is a perspective view of an apparatus for inspecting the substructure of a structural part according to a preferred embodiment of the invention.

Referring now to FIG. 1, a preferred embodiment of an apparatus 10 for inspecting the surface and the substructure of a structural part 14, such as a metallic or laminated composite aircraft or automotive part, is illustrated. The apparatus 10 supports a sensor 12 in a predetermined position relative to the surface of the part 14. The sensor 12 is adapted to inspect the surface and the substructure of a part 14, such as a metallic or laminated composite aircraft wing, to detect, for example, fatigue cracks and corrosion in a metallic wing, or delaminations, micro-cracks and voids in a laminated composite wing.

As shown, the apparatus 10 comprises a plurality of compliant fibers 16 which are arranged to contact the surface of the part 14. The apparatus 10 further comprises fiber support means 17 for fixing the plurality of compliant fibers relative to the sensor 12 such that the plurality of compliant fibers support the sensor above the surface of the part 14. Accordingly, the fiber support means 17 maintains the sensor 12 in a predetermined position, such as a predetermined standoff distance and a predetermined orientation, relative to the surface of the part 14 such that the sensor accurately detects the presence of structural flaws in the part.

Figure 2:
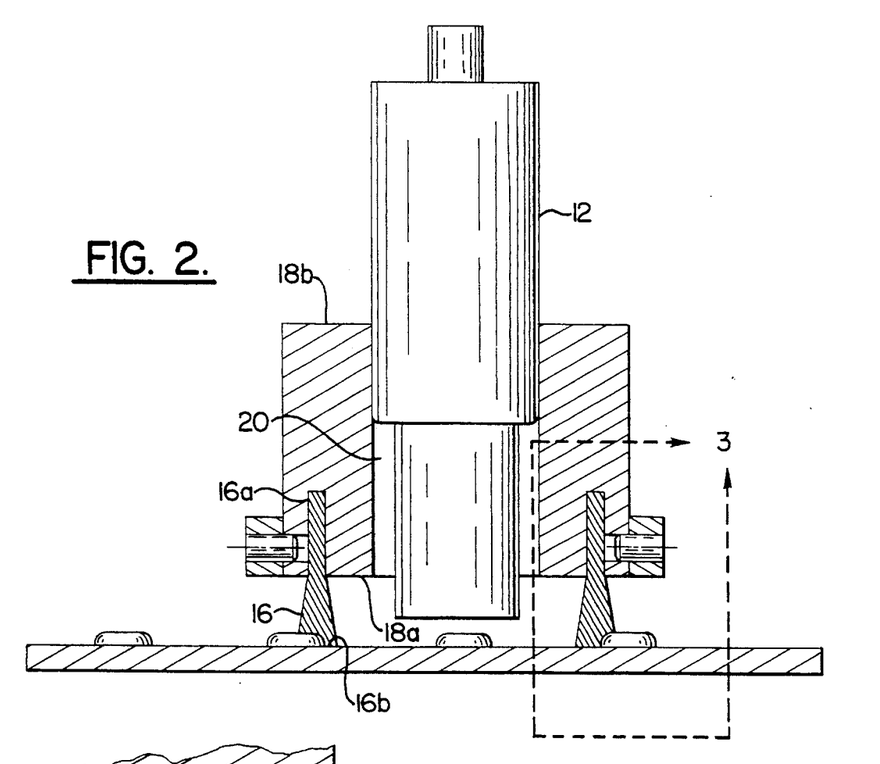
FIG. 2 is a sectional view of the apparatus of FIG. 1 taken along line 2—2.

In a preferred embodiment, the apparatus 10 embodies an NDT inspection apparatus. In this embodiment, the fiber support means 17 comprises a sensor housing 18, commonly referred to as a shoe, defining an internal cavity 20. As illustrated in FIGS. 1 and 2, the sensor housing 18 may be generally cylindrical so as to define an internal cavity 20 having a generally circular cross-section. However, the sensor housing 18 may have a variety of other shapes, such as rectangular, elliptical or square, without departing from the spirit and scope of the invention. The sensor housing 18 is typically made of acetal, but may be made of other materials without departing from the spirit and scope of the invention.

The sensor housing 18 has opposed first and second ends 18a and 18b, respectively, and is typically oriented such that the first end 18a is opposite the surface of the part 14 to be inspected. As best illustrated in FIG. 2, the internal cavity 20 defined by the sensor housing 18 is formed in the first end 18a of the sensor housing. In addition, the sensor 12 is disposed at least partially within the internal cavity 20 of the sensor housing 18. However, the sensor 12 may be disposed entirely within the internal cavity 20 of the sensor housing 18 without departing from the spirit and scope of the invention.

As known to those skilled in the art, the sensor 12 of apparatus 10 generates a signal which interrogates the surface and the substructure of the part 14 to detect the presence of structural flaws in the part. The sensor 12 may be a non-contact type sensor such that the sensor is not required to be in direct contact with the surface of the part 14. An example of a non-contact sensor is an eddy-current sensor which induces eddy currents in the part and measures the magnitude of the resulting eddy currents. Another example of a non-contact sensor is a laser sensor which probes the part with a plurality of laser pulses and, based upon the reflected laser energy, determines the presence of structural flaws in the part.

The sensor may also be a non-contact sensor which requires the presence of a fluid medium, or couplant, such as water, oil or gel, between the sensor and the surface of the part. An example of a non-contact sensor which requires a couplant is an ultrasonic pulse echo sensor which directs sound waves at the part and measures the frequency and magnitude of the reflected sound waves to detect the presence of structural flaws in the part.

Alternatively, the sensor may be a contact type sensor which requires direct contact between the sensor and the surface of the part to be inspected. An example of a contact sensor is an ultrasonic resonance sensor which directs mechanical energy at the surface of the part and measures the frequency and magnitude of the vibration of the part to detect the presence of structural flaws. Any type sensor for inspecting a structural part, however, may be used without departing from the spirit and scope of the invention.

Figure 4:
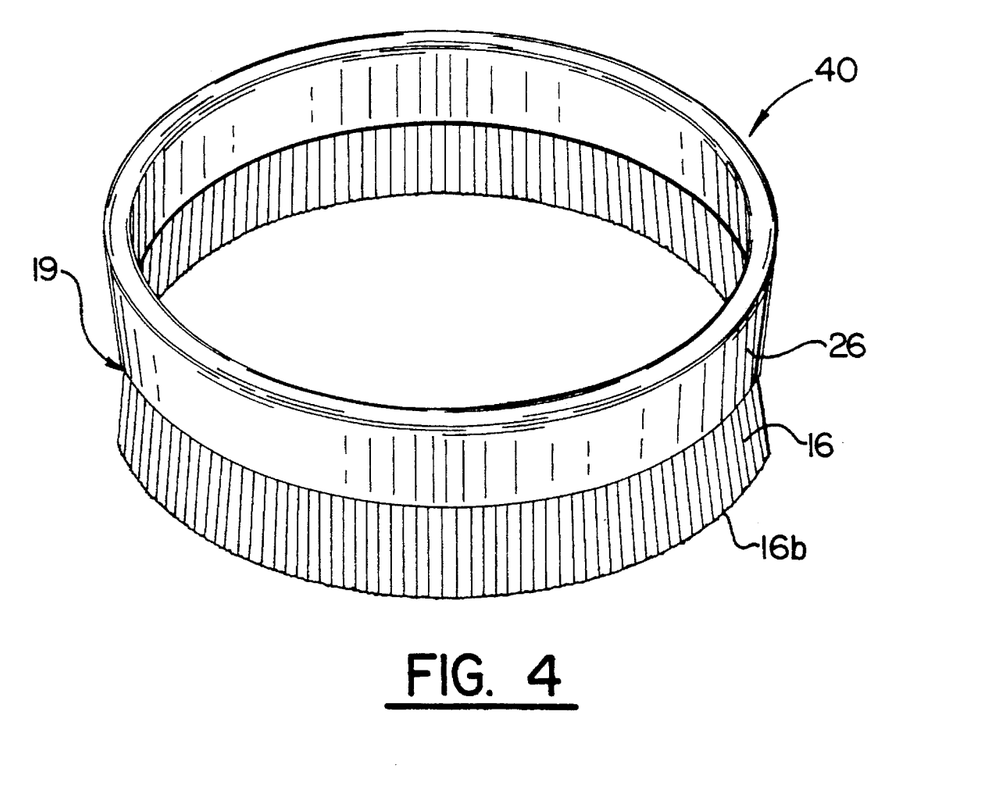
FIG. 4 is a perspective view of a compliant fiber assembly according to a preferred embodiment of the invention.

As illustrated, the plurality of compliant fibers 16 fixed by the fiber support means 17 of apparatus 10 extend outwardly from the first end 18a of the sensor housing 18 and circumferentially about the opening formed in the first end of the sensor housing. In the illustrated embodiment, the sensor housing 18 is generally cylindrical and the plurality of compliant fibers 16 extending circumferentially about the opening formed in the first end 18a of the sensor housing 18 define a compliant fiber ring 19 (FIG. 4). In addition, each of the plurality of compliant fibers 16 comprises a first end 16a and an opposed second end 16b.

Figure 3:
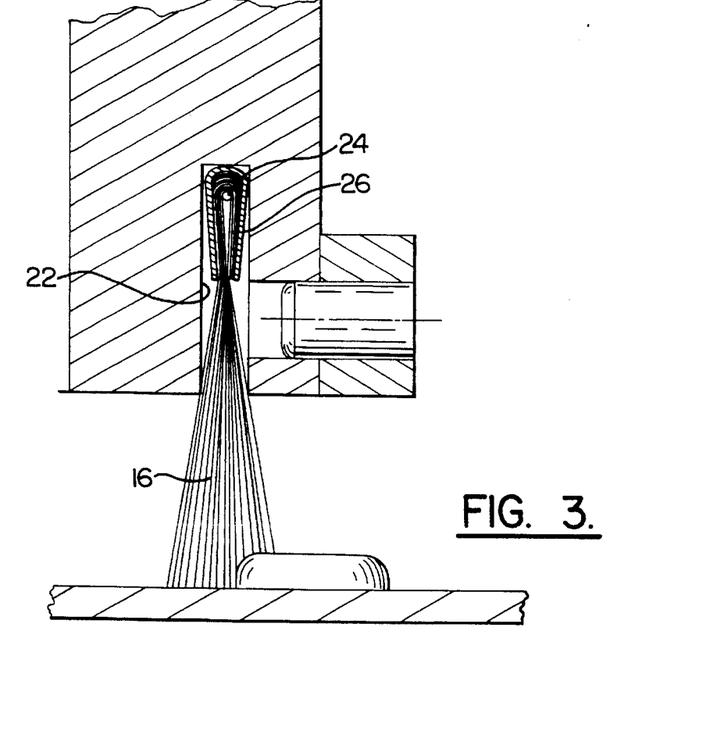
FIG. 3 is a detailed sectional view showing a preferred means for securing the compliant fiber assembly to the sensor housing of the apparatus of FIG. 1.

As illustrated in greater detail in FIGS. 3 and 4, the compliant fibers 16 may be secured within an annular channel 22, such as a C-shaped channel, defined by the opening formed in the sensor housing 18 adjacent the first end 18a. More particularly, a portion of the plurality of compliant fibers 16 may be wrapped about an annular core 24 which is sized and shaped so as to fit within channel 22 in a manner to be described. A formable metallic tape 26, such as an aluminum tape having a small thickness relative to the width of the channel 22, is folded over the portion of the compliant fibers 16 which are wrapped over the core 24 to secure the fibers to the core and thereby form an integral compliant fiber assembly 40. The fibers 16 may, however, be folded over and secured, for example, by stapling or bonding.

Thereafter, the compliant fiber assembly 40 is inserted within the channel 22 such that the plurality of compliant fibers 16 extend outwardly from the first end 18a of the sensor housing 18. It should be noted that although the plurality of compliant fibers 16 shown in the illustrated embodiments extend outwardly from the sensor housing 18 in a direction which is substantially parallel to the longitudinal axis of the housing and normal to the surface of the part 14, the plurality of compliant fibers may extend outwardly at any angle which best accommodates the requirements of the particular application and inspection method.

The compliant fiber assembly 40 is preferably press fit into channel 22 such that the frictional force between the assembly and the sidewalls of the channel fix the assembly securely relative to the sensor housing 18. The compliant fiber assembly 40 may also, however, be bonded, such as by an adhesive, or mechanically fastened, such as by a spring clip, into the channel 22 of the sensor housing 18 without departing from the spirit and scope of the invention.

The apparatus 10 further comprises a sensor housing support assembly 28 comprising a biasing means 29, such as a torsional spring, for applying a force to the sensor housing 18 in the general direction of the surface of the part 14 such that the second ends 16b of the plurality of compliant fibers 16 contact the surface of the part. As described hereinafter, the plurality of compliant fibers 16 support the sensor housing 18 above the surface of the part 14 such that the sensor 12 is maintained in the predetermined position relative to the surface of the part. In one advantageous embodiment, the plurality of compliant fibers 16 support the sensor housing 18 above the surface of the part 14 such that the sensor 12 is maintained at a predetermined standoff distance and a predetermined orientation relative to the surface of the part during an inspection.

As known to those skilled in the art, the output of a sensor 12 is most accurate when the sensor is maintained in a predetermined position relative to the surface of the part to be inspected. Thus, the sensor can detect the presence of structural flaws in the part without the influence of variations in the distance of the sensor from the surface of the part and the orientation of the sensor relative to the surface of the part which produce spurious results.

According to the invention, the plurality of compliant fibers 16 are adapted to flex laterally to accommodate obstructions on the surface of the part so that the sensor 12 is maintained in the predetermined position relative to the surface of the part 14. Thus, the apparatus 10 and, more particularly, the sensor 12 acquires more accurate signals which better indicate the presence of structural flaws in parts having obstructions on the surface, particularly in the vicinity of an obstruction.

As known to those skilled in the art, fasteners installed in aircraft wings and skins are typically countersunk into the part. Manufacturing specifications, however, may provide for a tolerance as large as, for example, 0.010 inches. Accordingly, the head of a fastener on an acceptable structural part may protrude as much 0.010 inches above the surface of the part. Some aircraft, particularly older aircraft, typically use round-head fasteners in wings and skins to join parts. Likewise, the head of a round-head fastener may protrude a significant amount above the surface of the part.

As known to those skilled in the art, obstructions on the surface of a part 14 can significantly distort the accuracy of the sensor 12 of apparatus 10 if the position of the apparatus relative to the surface of the part is upset as it passes over the surface obstruction. The accuracy of the sensor 12 is distorted because the position of the sensor relative to the surface of the part 14 is fixed with the position of the apparatus 10. According to the method and apparatus of the invention, however, the plurality of compliant fibers 16 flex laterally to accommodate the surface obstruction while maintaining the sensor 12 in the predetermined position relative to the surface of the part 14. Thus, the apparatus 10 is effective to inspect a structural part 14 having obstructions on the surface of the part, even in the vicinity of the obstruction. Accordingly, fatigue cracks, corrosion pillowing, delaminations, micro-crack and voids, for example, in the part 14, such as a raised fastener, doubler or lap joint, can be detected and repaired or replaced according to the method and apparatus of the invention.

The plurality of outwardly extending compliant fibers 16 have a predetermined compressive stiffness and a predetermined bending stiffness. The predetermined compressive stiffness of the plurality of compliant fibers 16 is sufficient to support the weight of the apparatus 10 and the downward force exerted by the biasing means 29. The predetermined bending stiffness is sufficient to overcome the frictional force applied to the apparatus 10 as it is moved over the structural part 14, but is compliant enough to permit the individual fibers to flex laterally to accommodate obstructions on the surface of the part while at the same time supporting the sensor housing 18 such that the sensor 12 is maintained at the predetermined standoff distance and in the predetermined orientation relative to the surface of the part 14.

In a preferred embodiment, the biasing means 29 urges the sensor housing 18 in the direction of the surface of the part 14 at a predetermined working load which conforms to the mechanical properties, cross sectional area and moment of inertia of the particular plurality of compliant fibers 16 selected for the inspection method used. The only requirement being that the resistance of the plurality of compliant fibers 16 to buckling, or the compressive stiffness, is sufficient to withstand the combined compressive forces of the weight of the apparatus 10 and the force exerted by the biasing means 29.

The compressive stiffness and the bending stiffness of the plurality of compliant fibers 16 is determined, at least in part, by the material, the mechanical properties, the cross sectional area and the cross sectional moment of inertia of the individual compliant fibers. In a preferred embodiment, each of the plurality of compliant fibers 16 is comprised of nylon. A plurality of compliant fibers made of individual nylon fibers and formed in various shapes is commercially available from SealE-Z Corporation.

As illustrated most clearly in FIG. 3 and as described above, each compliant fiber 16 is preferably secured to the first end 18a of the sensor housing 18 such that the respective second ends 16b of the plurality of compliant fibers extend outwardly a predetermined distance beyond the first end of the sensor housing. In one advantageous embodiment, the second end 16b of each of the plurality of fibers 16 extend the same predetermined distance beyond the first end 18a of the sensor housing 18. Thus, the plurality of compliant fibers 16 support the sensor housing 18 at a first predetermined distance above the surface of the part 14.

The plurality of compliant fibers 16 concurrently support the sensor 12 at a second predetermined distance, or standoff distance, above the surface of the part 14. As shown in FIG. 2, the second predetermined distance may be greater than the first predetermined distance. However, the second predetermined distance may also be less than the first predetermined distance, and, in some instances, the second predetermined distance may approach zero such that the sensor 12 is indirect contact with the surface of the part 14.

In addition, the first predetermined distance (the distance at which the sensor housing 18 is supported above the surface of the part 14) is preferably greater than the maximum height of the obstructions on the surface of the part. For example, in the exemplary embodiment described above in which countersunk or raised fasteners can protrude as much as 0.010 inches above the surface of the part 14, the first predetermined distance is sufficient such that the sensor housing 18 passes over the obstructions on the surface of the part without contacting the obstruction. Thus, the sensor housing 18 is protected from damage due to contact with an obstruction and the sensor 12 can inspect the part 14 in the vicinity of the obstruction.

Accordingly, the apparatus 10 allows the sensor housing 12 to be moved continuously over the surface of the part 14 such that the sensor 12 accurately acquires reflected signals from the surface of the part which are indicative of flaws in the part. The signals may be converted to a video image and displayed for the operator of the apparatus 10 such that structural defects in the part may be detected immediately.

Alternatively, the signals acquired by the sensor 12 may be stored for future display. Still further, the signals may be both converted into a video image and stored such that the operator has the option of reviewing the results of the inspection following the completion of the inspection process.

During the movement of the apparatus 10 over the surface of the part 14, the sensor 12 is maintained in the predetermined position relative to the surface of the part even when the apparatus is moved over an obstruction on the surface of the part. In particular, as described above, the sensor housing 18 is supported above the surface of the part by a plurality of compliant fibers 16 which flex laterally to accommodate the obstructions on the surface of the part without altering the predetermined position of the sensor 12. Thus, the apparatus 10 and, more particularly, the sensor 12 continuously acquires accurate signals that are indicative of defects in the part as the apparatus is moved over obstructions on the surface of the part.

The sensor housing support assembly 28 of the apparatus 10 is arranged to independently position the sensor housing 18 in at least two and, in some embodiments, three, mutually perpendicular directions. Thus, parts 14 having a compound curvature may be inspected while the sensor 12 is maintained in the predetermined position relative to the surface of the part. As illustrated in FIG. 1, the sensor housing support assembly comprises a yoke 30 having a pair of outwardly extending yoke arms 32 which are attached to opposed sides of the sensor housing 18. The attachment means of the yoke 30 permits the sensor housing 18 to rotate about the axis C in FIG. 1. In addition, the exterior surface of the sensor housing 18 preferably comprises a pair of opposed flat portions 18c which are adapted to rotatably attach the arms 32 of the yoke 30. As illustrated in greater detail in FIGS. 2 and 3, the pivot point defined by the rotatable attachment of the sensor housing 18 to the yoke 30 and through which axis C extends, is preferably below or longitudinally outward of the core 24 of the compliant fiber assembly 40 about which the plurality of compliant fibers 16 are folded.

The yoke 30 also comprises a neck 34. The neck 34 preferably comprises a rotatable connection, such as a shoulder bolt, between upper and lower neck segments 34a and 34b, respectively, such that the arms 32 of the yoke are adapted to rotate about axis B. The upper neck segment 34a of the yoke 30 is also rotatably connected to a mounting adapter 36. In particular, the yoke is adapted to rotate about the axis A relative to the mounting adapter 36.

As known to those skilled in the art, the mounting adapter 36 engages a frame assembly (not shown) which comprises means for moving the apparatus 10 transversely over the surface of the part 14. The frame assembly moves the apparatus 10 according to either an automated inspection process or a manual inspection process manipulated by an operator without departing from the spirit and scope of the invention. However, a preferred embodiment of the apparatus 10 further comprises a controller (not shown) for moving the sensor housing 18 over the surface of the part according to a predetermined inspection pattern. Thus, the part can be automatically inspected, according to the invention, even if the structural part to be inspected includes obstructions on its surface.

As described above, the upper neck segment 34a is preferably connected to the mounting adapter 36 by a gimble mechanism. The gimble mechanism, in turn, preferably comprises the biasing means 29 for biasing the yoke 30 in a clockwise direction about axis A such that the sensor housing 18 is urged in the direction of the surface of the part 14 as described above. In some embodiments, the sensor housing support assembly 28 may comprise means, such as a threaded member (not shown), which extends between the upper neck segment 34a of the yoke 30 and the mounting adapter 36 so as to limit or prevent relative movement about axis B. Accordingly, the apparatus 10 and, more particularly, the sensor housing 18 move in at least two and, in some embodiments, three, mutually perpendicular directions to conform the position of the sensor housing 18 to parts having a compound curvature such that the sensor 12 is maintained in the predetermined position, such as the predetermined standoff distance and the predetermined orientation relative to the complex curvature of the surface of the part 14.

As known to those skilled in the art, a number of sensors 12, such as ultrasonic pulse echo transducers, transmit signals to and receive signals from a part most efficiently via a couplant, such as a fluid medium. In particular, a couplant is preferably disposed between the sensor 12 and the surface of the part 14 to effectively couple the signals between the sensor and the part. Accordingly, the apparatus 10 of the invention may comprise a fluid reservoir defined at least partially by the internal cavity 20 of the sensor housing 18 and the plurality of compliant fibers 16. In this embodiment, a fluid, such as water, oil or gel, can be disposed within the fluid reservoir for efficiently coupling the signals transmitted between the sensor 12 and the surface of the part 14.

In one advantageous embodiment, the plurality of compliant fibers 16 are disposed in a plurality of circumferentially extending layers about the opening defined by the first end 18a of the sensor housing 18. Thus, in the embodiment of the apparatus 10 which comprises a cylindrical sensor housing, the plurality of compliant fibers preferably lie along each line extending radially outwardly from the center of the sensor housing 18. Thus, the plurality of circumferentially extending layers of the compliant fibers 16 generally contain the couplant within the fluid reservoir. By containing the couplant within the fluid reservoir, couplant need not be continually provided to the apparatus 10 but, instead, the fluid reservoir of the apparatus may be filled prior to an inspection and need thereafter only be replenished periodically.

Therefore, the plurality of compliant fibers 16 of the apparatus 10 of the invention support the sensor housing 18 at a predetermined distance from the part 14 such that the apparatus can move over obstructions on the surface smoothly and without being lifted and replaced on the surface of the part. In addition, the compliant fibers 16 are adapted to flex laterally to accommodate the obstructions on the surface of the part while maintaining the sensor 12 in a predetermined position, such as a predetermined standoff distance and a predetermined orientation, relative to the surface of the part. Thus, the sensor can reliably acquire signals indicative of flaws in the part, even in areas of the part which include obstructions on the surface, such as raised fasteners, doublers or lap joints which protrude above the surface of the part. In particular, the inspection method and apparatus of the invention can interrogate the part around the surface obstruction and can determine, for example, if defects are present in the surface or the substructure of the part. Accordingly, defects in the part can be detected and the part repaired or replaced as required.

In the drawings and the specification, there has been set forth a preferred embodiment of the invention and, although specific terms are employed, the terms are used in a generic That which is claimed is:

1. An inspection apparatus comprising:

a sensor housing defining an internal cavity opening through a first end of said sensor housing;

a sensor disposed at least partially within the internal cavity of said sensor housing for inspecting the surface of a structural part and for acquiring signals that indicate the presence of defects in the part;

a plurality of compliant fibers extending outwardly from the first end of said sensor housing and circumferentially about the opening defined by the first end of said sensor housing such that said sensor can transmit signals to and receive signals from the surface of the structural part independent of said plurality of compliant fibers, wherein each compliant fiber extends from a first end to an opposed second end, and wherein said plurality of compliant fibers have a predetermined compressive stiffness and a predetermined bending stiffness;

a sensor housing support assembly, operably connected to said sensor housing, for independently positioning said sensor housing in at least two mutually perpendicular directions such that parts having a compound curvature may be inspected, wherein said sensor housing support assembly comprises biasing means for urging said sensor housing in the direction of the surface of the part such that the respective second ends of said plurality of compliant fibers contact the surface of the part, wherein the predetermined compressive stiffness of said plurality of compliant fibers is sufficient to support said sensor housing above the surface of the part such that said sensor remains in a predetermined position relative to the surface of the part, and wherein the predetermined bending stiffness of said plurality of compliant fibers is sufficient to permit said compliant fibers to flex laterally to accommodate obstructions on the surface of the part while maintaining said sensor in the predetermined position relative to the surface of the part such that accurate signals which indicate the presence of defects in the part are acquired by said sensor.

2. An inspection apparatus according to claim 1 wherein said plurality of compliant fibers are secured to the first end of said sensor housing such that the respective second ends of said plurality of compliant fibers extend a first predetermined distance beyond the first end of said sensor housing so that said plurality of compliant fibers thereby support said sensor at a second predetermined distance above the surface of the part.

3. An inspection apparatus according to claim 1 wherein said plurality of compliant fibers are disposed in a plurality of circumferentially extending layers about the opening defined by the first end of said sensor housing.

4. An inspection apparatus according to claim 3 wherein said plurality of compliant fibers and the cavity defined by said sensor housing define a fluid reservoir, and wherein the inspection apparatus further comprises a fluid disposed within the fluid reservoir for coupling signals transmitted between said sensor and the surface of the part.

5. An inspection apparatus according to claim 1 further comprising a controller for moving said sensor over the surface of the part according to a predetermined inspection pattern such that the part is automatically inspected.

6. An inspection apparatus according to claim 1 wherein said sensor housing is cylindrical, and wherein said plurality of compliant fibers extending circumferentially about the opening defined by the first end of said sensor housing define a compliant fiber ring.

7. An apparatus for supporting a sensor in a predetermined position relative to the surface of a part, the apparatus comprising:

a plurality of compliant fibers extending longitudinally from a first end to an opposed second end, wherein the respective second ends of said plurality of compliant fibers are adapted to contact the surface of the part, and wherein said plurality of compliant fibers have a predetermined compressive stiffness and a predetermined bending stiffness; and compliant fiber support means for fixing the position of said plurality of compliant fibers relative to the sensor, wherein said compliant fiber support means comprises a sensor housing defining an internal cavity which opens through a first end of said sensor housing and within which the sensor is at least partially disposed, wherein said plurality of compliant fibers extend outwardly from the first end of said sensor housing and circumferentially about the opening defined by the first end of the sensor housing such that the sensor can transmit signals to and receive signals from the surface of the part independent of said plurality of compliant fibers, wherein the predetermined compressive stiffness of said plurality of compliant fibers is sufficient to support the sensor above the surface of the part such that the sensor remains in a predetermined position relative to the surface of the part, wherein the predetermined bending stiffness of said plurality of compliant fibers is sufficient to permit said compliant fibers to flex laterally to accommodate obstructions on the surface of the part while maintaining the sensor in the predetermined position relative to the surface of the part such that the sensor can accurately inspect the surface and the substructure of the part, and wherein said plurality of compliant fibers and the cavity defined by said sensor housing define a fluid reservoir which is adapted to receive and maintain a fluid in direct contact with the surface of the part for coupling signals transmitted between the sensor and the surface of the part.

8. An apparatus according to claim 7 wherein said plurality of compliant fibers are secured to said compliant fiber support means such that the respective second ends of said plurality of compliant fibers extend a first predetermined distance outwardly therefrom so that said plurality of compliant fibers support the sensor at a second predetermined distance above the surface of the part.

9. An apparatus according to claim 7 wherein said compliant fiber support means fixes the relative positions of said plurality of compliant fibers according to a predetermined pattern.

10. An apparatus according to claim 7 wherein said sensor housing is cylindrical, and wherein said plurality of compliant fibers extending circumferentially about the opening defined by the first end of said sensor housing define a compliant fiber ring.

11. A method of inspecting the surface of a structural part with an inspection apparatus comprising a sensor housing defining an internal cavity opening through a first end of said sensor housing, a sensor disposed at least partially within the internal cavity of said sensor housing, and a plurality of compliant fibers extending outwardly from the first end of said sensor housing and circumferentially about the opening defined by the first end of said sensor housing, the method comprising the steps of:

interrogating the surface of the part with the sensor;

obtaining signals indicative of the presence of structural defects in the part based upon the interrogation of the part;

moving the inspection apparatus along the surface of the part while continuing to interrogate the surface of the part;

independently positioning the sensor housing in at least two perpendicular directions to thereby enable a structural part having a compound curvature to be inspected, wherein said independently positioning step comprises the step of maintaining the sensor in a predetermined position relative to the surface of the part as the inspection apparatus moves over an obstruction on the surface of the part, said maintaining step comprising the steps of:

urging the sensor housing in the direction of the surface of the part such that the plurality of compliant fibers contact the surface of the part;

supporting the sensor housing above the surface of the part with the plurality of compliant fibers which have a predetermined compressive stiffness sufficient to support the sensor in a predetermined position relative to the surface of the part; and bending a portion of the compliant fibers which have a predetermined bending stiffness sufficient to permit the compliant fibers to be bent laterally to accommodate the obstruction on the surface of the part without altering the predetermined position of the sensor relative to the surface of the part such that accurate signals which indicate the presence of defects in the part are obtained.

12. A method according to claim 11 wherein the inspection apparatus further comprises a fluid reservoir defined at least partially by the internal cavity of the sensor housing and the plurality of composite fibers, and wherein the method further comprises the steps of:

maintaining fluid within the fluid reservoir and in direct contact with the surface of the part; and coupling signals transmitted between the sensor and the surface of the part with the fluid disposed within the fluid reservoir.

13. A method according to claim 11 wherein said moving step comprises the step of moving the sensor over the surface of the part according to a predetermined inspection pattern such that the part is automatically inspected.

* * * * *